United States Patent [19]
Beran

[11] Patent Number: 4,516,293
[45] Date of Patent: May 14, 1985

[54] CLAMPING STRUCTURE

[76] Inventor: Anthony V. Beran, 1472 La Loma Dr., Santa Ana, Calif.

[21] Appl. No.: 488,057

[22] Filed: Apr. 25, 1983

Related U.S. Application Data

[63] Continuation-in-part of Ser. No. 256,698, Apr. 23, 1981.

[51] Int. Cl.³ .............................................. B65D 63/00
[52] U.S. Cl. .............................. 24/16 PB; 24/17 AP; 24/30.5 P; 128/207.17; 128/DIG. 26
[58] Field of Search ............. 24/16 PB, 16 R, 17 AP, 24/30.5 P; 128/207.17, 348.1, DIG. 26; 604/179

[56] References Cited
U.S. PATENT DOCUMENTS

| | | | |
|---|---|---|---|
| 2,908,269 | 10/1959 | Cheng | 128/DIG. 26 |
| 3,339,246 | 9/1967 | Geisinger | 24/16 PB |
| 3,339,247 | 9/1967 | Geisinger | 24/16 PB |
| 3,513,508 | 5/1970 | Modeme | 24/16 PB |
| 3,774,616 | 11/1973 | White et al. | 128/DIG. 26 |
| 3,837,047 | 9/1974 | Bunnell | 24/16 PB |
| 4,114,626 | 9/1978 | Beran | 128/DIG. 26 |
| 4,249,529 | 2/1981 | Nestor et al. | 128/207.17 |
| 4,389,754 | 6/1983 | Sohma | 24/17 AP |
| 4,435,881 | 3/1984 | Yamaguchi et al. | 24/16 PB |
| 4,439,896 | 4/1984 | Matsui | 24/16 PB |

Primary Examiner—Victor N. Sakran
Attorney, Agent, or Firm—Grover A. Frater

[57] ABSTRACT

A tube holder includes a clamp formed by a clamp base and a wrap-around strap. The strap is fixed at one end to the base and, after wrapping around the tube, is locked to the clamp base at a point along its length in a double locking system.

7 Claims, 17 Drawing Figures

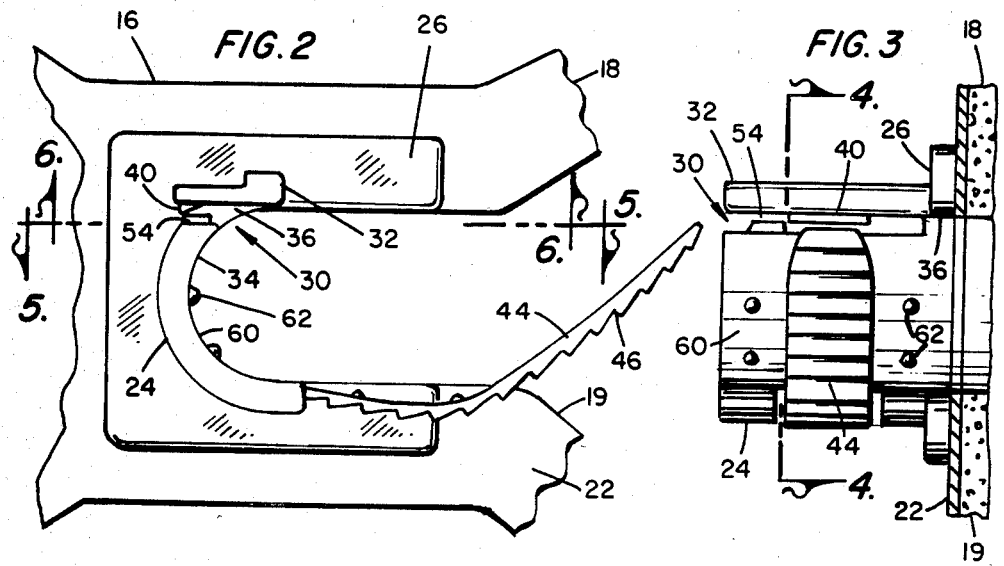
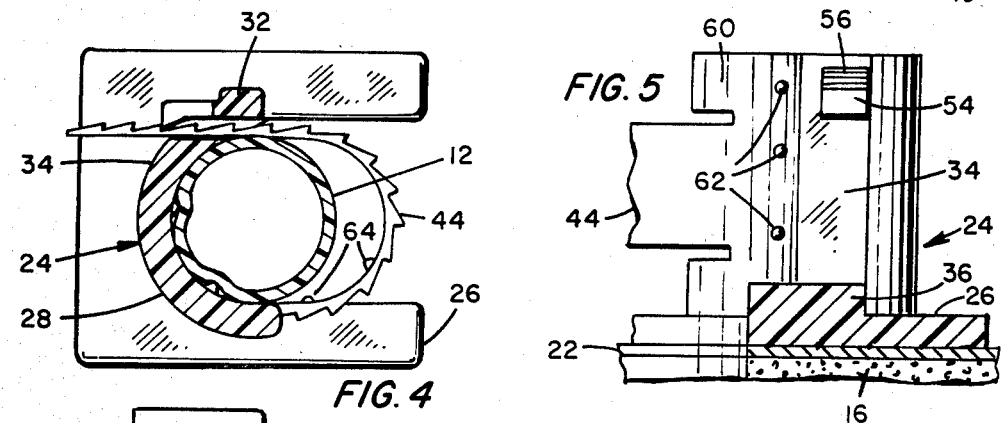
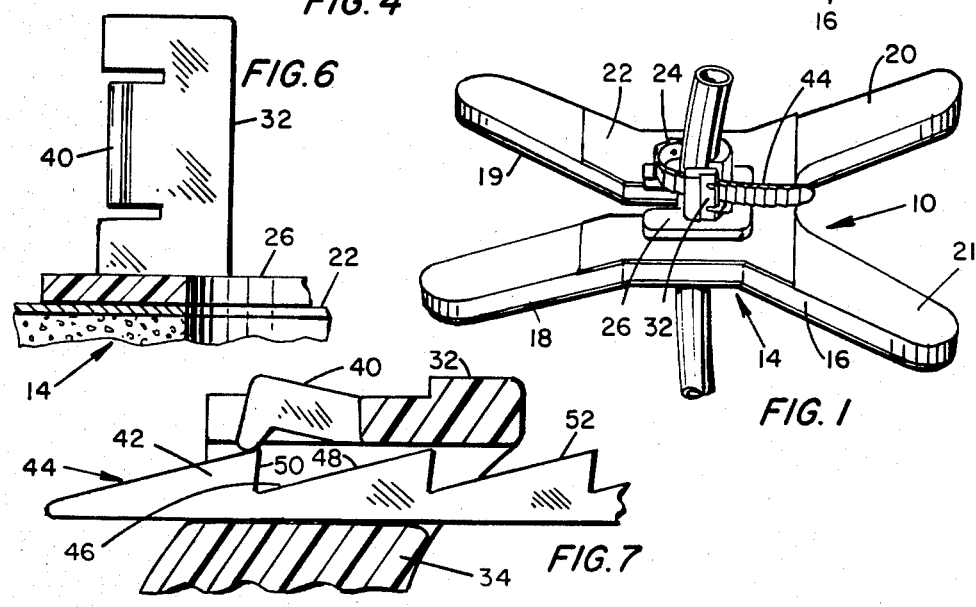
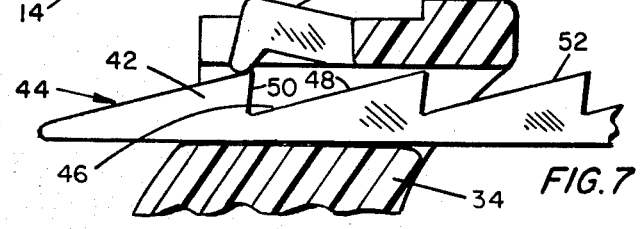

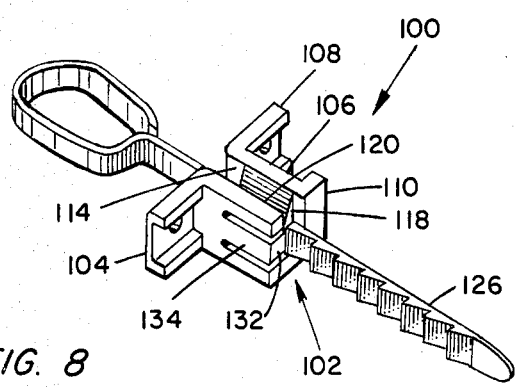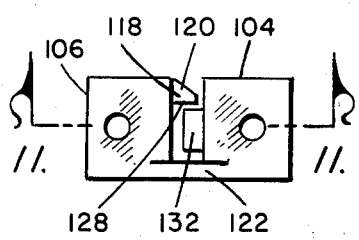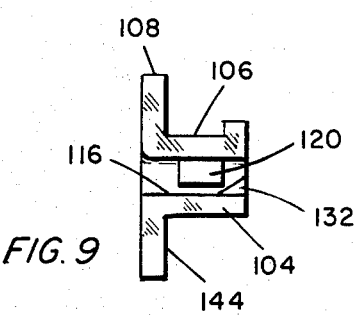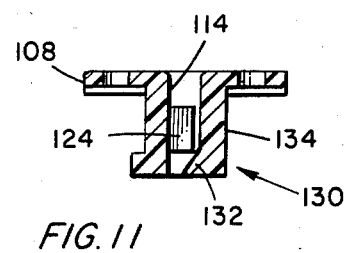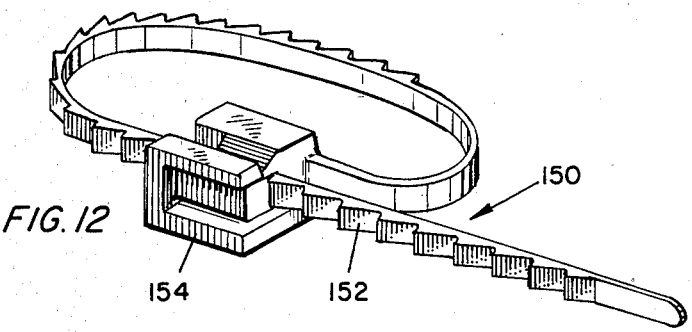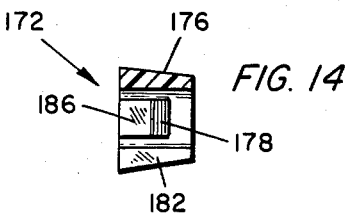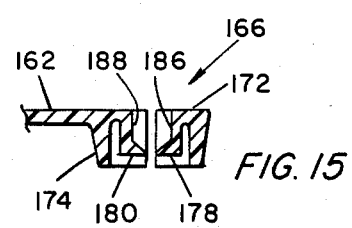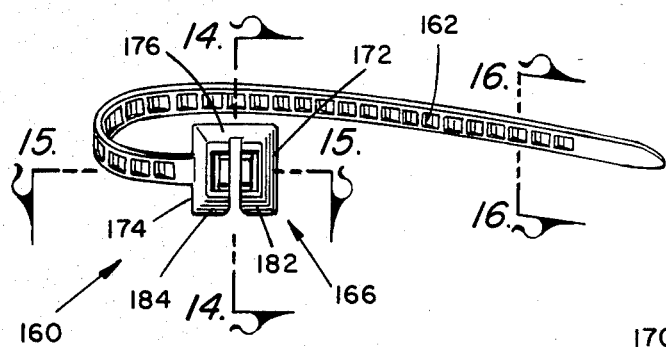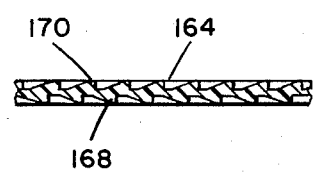

CLAMPING STRUCTURE

CROSS-REFERENCE TO RELATED APPLICATION

This application is a continuation-in-part of U.S. application Ser. No. 06/256,698, filed Apr. 23, 1981 for TUBE HOLDER.

TECHNICAL FIELD

This invention relates to improvements in tube holders and ties, and particularly to clamping structures for tube holders, and particularly to dual-locking ties.

BACKGROUND ART

While the invention has other applications, one of the most important is to hold endotracheal, gastrointestinal and other tubes, and to fix their position relative to the patient in which such tubes are inserted. Those tubes enter at the patient's nostril or mouth and must be fixed to the patient to insure against unwanted change in the degree of insertion. If the patient is going to be able to move, the point of fixation must be right at the nose or mouth. Most of the practical holders include an adhesive patch to which a tube clamp is fixed.

A widely accepted and successful tube holder is shown in Beran U.S. Pat. No. 4,114,626. Its clamp is a two-piece structure which is easily applied to, and readily removed from, patient and tube. It is intended primarily for use with infants—with small diameter tubes and a limited number of sizes. Each holder is designed for only one tube size.

The ideal tube holder for adult patients would be adjustable or otherwise, arranged so that one holder would accommodate many tube sizes. The need for positive clamping is no less, and, indeed, is often greater in the case of adult patients because adult patients move more and they subject the tube and holder to greater forces than do infants.

Another requirement for the adult tube holder is that it be easy for the medical technician and nurse to install and to remove, and difficult for the patient to remove. While difficulty of removal by a patient is not an often needed feature, it is important in certain cases. Thus, the ideal tube holder is one that exhibits that difference in case of removal.

These holders include an adhesive surface or other attachment means including straps and hook and fabric arrangements, and are used next to the patient's nose and mouth. Cleaning is not practical so the holder is a throw-away product. The ideal holder is designed for production at very low cost, and presents minimum quality, storage, sterilization and packaging problems. The Beran holder of Pat. No. 4,114,626 meets these tests but, at least in adult sizes, the holder provided by this invention is best.

Many applications do not require the adhesive surface. The novel locking arrangement of the invention provides a clamping structure having wide utility for binding and clamping.

DISCLOSURE OF INVENTION

The invention provides a tube holder which is adjustable in that it can be used to hold tubes that have any of a number of different sizes. It provides a reliable, inexpensive, easily used holder, the holding action of which is positive. To provide a device with those characteristics is an object of the invention.

In the Beran two-piece locking system a locking cylinder is forced over a split cylinder which surrounds the tube. The mating surfaces of the locking cylinder and the holding cylinder are relatively tapered. The result is that the clamping action between tube and holder is applied over a relatively large area of the tube. The tapered shape provides a mechanical purchase that permits gripping of the tube with a larger force than is needed to press the locking and holding cylinders together.

The advantage of that system of force multiplication is lost when the two-piece design is replaced with a locking system which can be molded as a single unitary device. The invention overcomes that loss by a distortion of the cross-sectional shape of the tube. The holding structure is arranged so that the tube is pressed to slightly oval shape at the region at which it is engaged by the holder. That is augmented, or even replaced, by projections that extend from the holder into engagement with the exterior wall of the tube. In preferred form those projections do not pierce the tube wall, but merely distort its shape in small degree.

The relatively tapered surfaces of the Beran two-piece holder engage one another over a large area such that friction alone provides adequate locking force. The one-piece arrangement or capability, in the invention, utilizes a different arrangement. One part of the holder cooperates with another part to embrace the tube, and the two parts are positively locked together. They are locked as bolt and latch. Matching conformations, one on one of the two parts and the other on the other part, serve one as the latch and the other as the bolt. The lock in the invention can be closed by either of two motions which differs in direction. The direction of one is perpendicular to the direction of the other. The conformation that is the latch in one locking motion is the engaged conformation in the other locking motion. In the preferred forms of the invention, either motion, or both, is available to close the lock and hold the tube fast in the embrace of the two parts.

Adjustability is provided by a duplication of at least one of the two conformations at spaced points along a surface of that one of the two parts on which the conformation is formed. In preferred form one of the two parts is a strap and the conformation on the strap is reproduced at spaced points along its length. The strap serves as the bolt in a second lock.

In the second lock the bolt, or strap, is engaged in a keeper. In the preferred form of the invention the closure of the second lock is accomplished by either of the above described motions as the first lock is closed. The first lock prevents opening of the second in one of the two motion directions, and the second prevents opening of the first lock in the second of the two motion directions. Thus, a tube once locked in place can be released only by unlocking the first lock first whereupon the second lock can be unlocked.

A variety of structures may be employed in practice of the invention, and not all of its features are required to realize the advantages of the invention.

In a broader sense, the invention can be thought of as a lock in which the bolt can enter the keeper in either sidewise or endwise direction, and is prevented from withdrawal by a lock in one direction and a latch in the other. Further, the bolt may be removed by withdrawal of at least one of the lock or latch.

BRIEF DESCRIPTION OF THE DRAWINGS

In the drawings:

FIG. 1 is an isometric showing of a holder, in which the invention is embodied, assembled with a tube, the holder clamp being shown as it appears during locking and unlocking of the clamp;

FIG. 2 is a top view of a fragment of the holder of FIG. 1;

FIG. 3 is a side view of the fragment of FIG. 2;

FIG. 4 is a sectional view taken on line 4—4 of FIG. 3 except that the end of the strap is shown to be inserted in the keeper and the tube wall deformed as if held tightly in the clamp;

FIGS. 5 and 6 are cross-sectional views taken on lines 5—5 and 6—6, respectively, of FIG. 2;

FIG. 7 is a fragmented, cross-sectional view looking down on the strap retainer structure and strap on a plane just above the upper edge of the strap and just below the double lock projection;

FIG. 8 is a fragmented, isometric view of another embodiment of the invention, this one arranged for automatic application assembly;

FIG. 9 is a top plan view of the lock of the embodiment of FIG. 8;

FIG. 10 is a view in rear elevation of the lock of the embodiment of FIG. 8;

FIG. 11 is a fragmented, cross-sectional view taken on line 11—11 of FIG. 10;

FIGS. 12 and 13 are isometric views of two more embodiments of the invention;

FIGS. 14, 15 and 16 are cross-sectional views taken on lines 14—14, 15—15 and 16—16, respectively, of FIG. 13; and FIG. 17 is a cross-sectional view taken on line 17—17 of FIG. 16.

DESCRIPTION OF THE PREFERRED EMBODIMENT

The preferred embodiment of the invention includes most of its features. The specific form of those features have been selected as preferred for a nasal/oral tube application for the invention. The application has been selected on the basis of its importance. In other applications other specific forms might be considered preferable.

In FIG. 1 the holder 10 is shown assembled on a length of tubing 12. The tube is made of transparent plastic. It is resilient and relatively soft. It has a diameter which is within the range of tube diameters commonly used in intubating medical patients, and it is a commonly used type.

The holder 10 includes a patient attachment section 14 by which it is fixed to the face of the patient adjacent his mouth or nostril. Section 14 includes a central portion 16 from which four strap arms extend to form an X-shape. The strap arms are designated 18, 19, 20 and 21 for identification. The lower side of section 14, the side that is hidden from view in FIG. 1, is covered with a layer of pressure sensitive adhesive material by which section 14 is made to adhere to the patient's skin. A layer 22 of pressure adhesive tape material overlies central portion 16 of section 14 and is bonded to the pliant plastic foam material which forms the central portion 16 and the arms 18, 19, 20 and 21.

The upper portion 24 of the holder is the tube clamp section. It is joined, in this case it is formed integrally, with a flange 26 which is interposed between the clamp section 24 and the patient attachment section 14. The lower face of the flange 26 is bonded to the upper face of the tape material layer 22. The adhesive that joins the flange to layer 22 is strong. The margins of the flange need not extend much beyond the area occupied by the lower end of the clamp whereby the patient attachment portion is easily bent out of the plane of the flange close to the clamp section.

The clamp section includes a base which is slotted at one side from the end opposite the flange 26. The slot extends entirely through from one side of the base to the other in a plane perpendicular to the plane of the flange. The slot is almost as deep as the base is high. Thus, the base can be considered as consisting of the semi-circular segment 28 at one side of the slot 30 (FIGS. 2 and 3) and the latch post 32. Alternatively, the latch post 32 and the opposing structure 34 can be thought of as arms of a U-shaped member connected by connecting section 36. One arm, arm 34 in this case, is then integrally formed with the base 24.

A latch 40 is fixed to the latch post 32 such that it extends into the slot 30. It need not actually be in the slot but could be positioned beyond the slot itself. Its position lengthwise of the slot is less important than that its normal, relaxed position is in the plane of the slot. In this embodiment the latch is about one-third or one-half as wide as the slot is deep and it is positioned in the midregion of the slot's depth.

The post 32 is formed of resilient material. It can be bent away from the base 24, and more particularly from "arm" 34 to widen the slot 30. The latch 40 is formed integrally with post 32. Spaced slots in the latch post define the latch as a cantilever the end of which is formed as a triangular prism. It is the triangular part that extends into the plane of the slot. Being formed of resilient material, it can be cantilevered back out of that plane as it is shown to be in FIG. 7 by the portion 42 of strap 44.

The strap can be considered to be a bolt which can be moved in the direction of its length through the slot, to the left in FIGS. 4 and 7 of the drawing. The conformation 46 on the strap is a triangular slot into which the latch 40 will spring if the strap 44 is moved leftward in FIG. 7 to bring the conformation 46 into position opposite to a triangular portion of the latch. Conformation 46 is formed by a sloping surface 48 and a near perpendicular surface 50. It will be apparent that the strap can be moved to the left in FIG. 7. The latch will be cammed back by the sloping surface 46 and 52 of the next conformation. However, once the strap has been inserted to a degree that permits entry of the latch into a notch of the strap, the strap is locked against withdrawal by rightward movement.

These two conformations, the triangular projection of the latch and the triangular notch of the strap, constitute the first lock in this embodiment. The position of the conformations can be reversed and their shape can be other than triangular, and other variations are possible. However, it is a feature that the two conformations can be interlocked either by movement of the strap through the slot from one side toward the other or by matching the conformations by movement of the strap while positioned above the latch and then moving the strap down into the slot until the conformations interlock or mesh.

Such downward motion is impeded by a projection which extends into the slot above the latch from one or the other side of the slot. It is preferred that the projection extend from arm 34 opposite the latch post arm 32. It is numbered 54 in the drawings. The upper surface 56 slopes downwardly into the slot but the lower surface is perpendicular to the plane of the slot. The projection is positioned above the latch 40. It does not interfere with insertion of the end of the strap into the slot or with movement of the strap through the slot in the direction of the length of the strap. However, the projection does interfere with movement of the strap vertically in and out of the slot from and to the open end of the slot. Motion of the strap into the slot past the projection is possible because of the sloping upper surface and the resilience of the latch post. The side of the strap being forced down against the sloping surface, the strap will be cammed against the latch post. The post will be forced away from the projection until the strap can slide down past the projection. If a strap notch is aligned with the latch the strap continues down. If not aligned the strap is pushed through the slot until there is alignment.

Removal of the strap upwardly in the slot past the projection is another matter. The projection's lower face is perpendicular. The strap is locked in place by the lower face as a second lock. It can be removed only by widening the slot, in this embodiment by bending the latch post. That can be done by pulling the post with one finger while lifting the strap with another or by forcing the end of the strap against the post and upwardly simultaneously to bend the post and force the strap clear of the latch and projection.

In the preferred embodiment the semi-circular part 28 of the base is only approximately semi-circular. The other end of the strap 44 is fixed to the part 28 at the side opposite the U-shaped strap keeper. It must be, and is, flexible and it exhibits some resilience. In the preferred embodiment it is molded integrally with the remainder of the tube clamp section and along with latch post 24 forms a part of that section. In the preferred embodiment the strap is molded such that it occupies substantially the position shown in FIGS. 2 and 3 of the drawing. The end extends away from the base generally parallel at first with the plane of the slot, and then it curves inwardly toward the plane of the slot. As best shown in FIGS. 2 and 3 the strap is relatively wide and the triangularly shaped conformation 46 is repeated at spaced points along substantially all of its length. It lies in a plane that is parallel with the plane of the base 26. Those conformations extend entirely across the width of the strap and are parallel to the side walls of the slot and to the inner surface 60 of the semi-circular base 28.

Surface 60 extends lengthwise over the length of the base. As best shown in FIG. 1, the patient attachment section 14 and the flange 26 are cut away from the region which is faced by surface 60. While the end of the strap 44 extends into that region, the way is clear to move a section along the length of a tube between arms 18 and 19 past the end of the strap 44 and against surface 60. To clamp it in place the free end of strap 44 is wrapped around to the region of the latch post 32. The end of the strap may be inserted into the slot 30 below projection 54 and then pushed through the slot, ratcheting the latch until the strap embraces the tube 12 tightly enough to cause deformation of the tube wall by the several small projections 62 which extend from surface 60. The deformation is depicted in FIG. 4. In that figure the strap is not drawn into tight embrace around the tube 12 but the normally circular tube wall is shown to be deformed by the projections on wall 60 as it would be if the strap was tight. Additional projections 64 are formed on the side of the strap toward the tube and they, too, cause a slight deformation of the tube wall when the strap is drawn tight.

It is not necessary to "thread" the end of the strap into the slot 30 from the side. It is more convenient to lift the end of the strap around the tube and over the slot. The edge of the strap is easily directed into the slot as it is shown to be in FIG. 1. Pressing down gently but firmly at the side of the strap beyond the latch post forces the strap to cam the post away from projection 54 and down to the latch. Matching the latch and a groove of the strap is easily accomplished with a minimum of finger manipulation. When the conformations are aligned the strap is forced down past the projection 54. FIG. 4 represents the condition at that point in the process. The strap is locked in the strap retainer so that it cannot be withdrawn from the side or the end of slot 30. However, the strap can be forced farther through the slot by ratcheting past the latch 40 until the strap is tight against the tube 12 and the tube wall is deformed by both sets, 62 and 64, of projection.

The holder can be attached to the patient before or after assembly of the tube with the clamp and clamping can be completed at any point in the process.

When the clamp is to be opened, either for removal or adjustment of degree of tube insertion, the end of the strap 44 is lifted up to separate the latch and strap conformations, as shown in FIG. 1. To do that the slot must be opened to permit the strap to slide between the projection 54 and post 32. Fingernail pressure on the post, or applying outward and upward force on the end of the strap, will provide the required slot opening.

While the double locking arrangement seems complex in the abstract, it is convenient to use, and it can be accomplished in a relatively simple, easily manufactured, reliable structure.

A form intended for installation by a robotic device is illustrated in FIGS. 8, 9, 10 and 11. In this case the clamping device, or lock, 100 has no flange corresponding to flange 26 of the first described embodiment. The base, or keeper, 102 is formed by a latch post 104, and an opposing, locking post 106. A connecting web 122 holds them in spaced relation. The outer side of the post 106 is channel-shaped. The channel side walls have the form of ribs 108 and 110. At this inner side 114, the locking post includes an integrally formed lock 118. The lock is a projection which extends toward the inner surface 116 of the latch post 104. The upper face 120 of the lock slopes downwardly as best shown in FIG. 10, into the space between the two posts toward the connecting web 122 that joins the two posts and, together with them, forms the U-shaped base 102.

The upper face is sloped downwardly to facilitate the sidewise insertion of a bolt which, in this case, is shown as a strap 126, into the space between the posts. The lock extends across the space sufficiently far so that the distance between the lock 118 and inner face 116 of the post 104 is less than the width of the strap 126. The strap can be inserted only if the separation between the lock and the wall 116 is increased. In this embodiment, the entire structure is formed of a material that is resilient. It is deformable and exhibits renitance to return to original shape. In this case the arms 104 and 106, the web 122, and the stop 118 all yield when the strap is forced past the stop into the space between the arms. The several parts of the base 102 yield because the strap functions as a cam follower and the sloping face of the stop functions as a cam. The lower face of the stop is shaped so that it will not serve as a cam. In this case the lower face 128 is flat and perpendicular to walls 114 and 116.

The side entry feature is particularly useful when using automatic machinery for assembling the clamp on an application structure. It is far less complicated to slide the strap into the base sideways than to thread the end of the strap into a slot. The former can be accomplished without changing the point at which the mechanism grasps the strap. This particular design is arranged for clamping a flow tube to a short stanchion using a manipulator robot.

As in the embodiment first described, this one includes a latch which engages conformations on a strap. The conformations in this case have saw-tooth form. They serve as cams to cam the latch member 130 back toward face 116 of post 104. The latch member is integrally formed with the base. It comprises a latch dog 132 at the end of a resilient arm 134. The arm biases the dog toward wall 114 of the base so that it will spring in back of each tooth if the strap 126 is pulled through the base slot. To remove the clamp, the arms 104 and 106 are simply forced apart until the stop 118 clears wall 116 enough to permit the strap to pass sideways between them.

The lateral extensions 108 and 144 serve two purposes. The attachment robot holds the clamp by holding one of the extensions. In this case they are ribbed or channel-shaped to fit into the assembly tool holder. If the clamp is to be removed, the extension serves as a handle or lever for drawing arm 104 away from arm 106 until the strap can be freed.

The version 150 of the invention that is shown in FIG. 12 has its strap or bolt 152 integrally formed with the base or keeper 154. Otherwise, it is similar to the embodiment of FIG. 8.

The lock 160 of FIG. 13 is designed to serve as an inexpensive "tie" that can be used over and over. The strap 162 is formed with a ridge 164 at each edge. Between those ridges the strap is formed with conformations at both sides which are engageable with the latch structures of the base or keeper 166. That the latch engaging conformations are formed on both sides is best shown in FIG. 17. For identification, one conformation is numbered 168 and another, on the opposite side, is numbered 170.

The keeper is generally U-shaped as best shown in FIG. 13. The arms of the U are numbered 172 and 174, respectively. The bottom of the U is numbered 176. There is a latch dog and a stop associated with each of arms 172 and 174. The latch dogs are best seen in FIGS. 15 where the latch associated with arm 172 is numbered 178. The other is numbered 180. The stops are best seen in FIG. 13. The stop 182 is formed integrally with arm 172. Stop 184 is formed integrally with arm 174.

The separation of the stops 182 and 184 is less than the width of the strap. When the strap is inserted edgewise between the arms 172 and 174 and forced between them, the arms are cammed apart to permit entry. In this design the spacing between the two latch dogs, in relaxed condition, is substantially the same as the spacing between the two locks. The latch dogs are separated when the locks are separated.

The latch dogs are mounted at the end of a resilient arm numbered 186 in the case of latch 178, and 188 in the case of latch 180. As in the case of the other designs, the keeper and the strap are resilient.

Although I have shown and described certain specific embodiments of my invention, I am fully aware that many modifications thereof are possible. My invention, therefore, is not to be restricted except insofar as is necessitated by the prior art.

I claim:
1. In a locking structure for a clamp:
   bolt means for locking cooperation with a surface conformation on a keeper;
   a keeper formed by two members spaced to provide an opening between them;
   a latch carried by the keeper and resiliently mounted on one of said members for movement in said opening;
   said latch being biased to a position in said opening such that entry of the bolt means into the space between said members requires mating of said conformation and said latch or retraction of the latch;
   said members being capable of being spread apart and in which a projection extends into said space from one of said members sufficiently to require spreading of said members to permit entry of the bolt means into said space by arranging said conformation and latch in mating position.
2. The invention defined in claim 1 in which said projection is formed with a sloping surface which is sloped to greater extension into said space in the direction in which the bolt means is moved to entry into said keeper when conformation and latch are aligned.
3. The invention defined in claim 2 in which said two members are joined at a point along their length such that said space between said members consitutes a slot, said latch being mounted at a point in said slot closer than said projection to the juncture between said members.
4. A locking structure comprising:
   a bolt having an end and a side;
   a keeper shaped to define a repository for the bolt having a first normally blocked entryway to receive the bolt endwise, and a second normally blocked entryway to receive the bolt sidewise;
   a lock extending into one of said first and second entryways and a latch extending into the other entryway; and
   camming means carried by one of said keeper or said bolt for camming open one of said entryways sufficiently to permit entry of the bolt, and camming means carried by one of said keeper and said bolt for camming open the other of said entryways sufficiently to permit entry of the bolt.
5. The invention defined in claim 4 in which said keeper is formed of a resilient material which yields in response to cam action.
6. A locking structure comprising:
   a keeper which defines a repository for a bolt and a first entryway for endwise insertion of the bolt and a second entryway for sidewise insertion of the bolt;
   a locking member and a latch associated with respective ones of said first and said second entryways and means for withdrawing at least one of said locking member and said latch to permit removal of a bolt from said repository;
   said keeper being U-shaped, the repository for a bolt being defined by the space between the arms of the U-shape;
   said locking member and said latch being formed on one arm of the U-shape; and a second locking member and a second latch, the second locking member and the second latch being formed on the other arm of the U-shape.

7. The invention defined in claim 6 which further comprises a strap, the strap being formed with a plurality of latch engaging conformations on each of its two sides.

* * * * *